(12) United States Patent
Gatzemeyer et al.

(10) Patent No.: US 8,523,888 B2
(45) Date of Patent: Sep. 3, 2013

(54) ORAL CARE IMPLEMENT

(75) Inventors: John J. Gatzemeyer, Hillsborough, NJ (US); Douglas J. Hohlbein, Pennington, NJ (US)

(73) Assignee: Colgate-Palmolive Company, New York, NY (US)

( * ) Notice: Subject to any disclaimer, the term of this patent is extended or adjusted under 35 U.S.C. 154(b) by 656 days.

(21) Appl. No.: 11/612,118

(22) Filed: Dec. 18, 2006

(65) Prior Publication Data

US 2008/0147104 A1 Jun. 19, 2008

(51) Int. Cl.
*A61B 17/24* (2006.01)

(52) U.S. Cl.
USPC .............. 606/161; 15/110; 15/111; 15/187; 15/188

(58) Field of Classification Search
USPC .............. 606/161; 433/142, 143, 6, 37, 80, 433/216; 132/309; 15/121, 110, 111, 186–188
See application file for complete search history.

(56) References Cited

U.S. PATENT DOCUMENTS

| | | |
|---|---|---|
| 585,358 A | 6/1897 | Gould |
| 726,727 A | 4/1903 | Mills |
| 864,054 A | 8/1907 | Abrams |
| 907,842 A | 12/1908 | Meuzles |
| 1,002,468 A | 9/1911 | Strangman |
| 1,006,630 A | 10/1911 | Clarke |
| 1,126,139 A | 2/1915 | Hoffman |
| 1,142,698 A | 6/1915 | Crumbaugh |
| 1,153,409 A | 9/1915 | Wheeler |
| 1,191,558 A | 7/1916 | Blake |
| 1,251,250 A | 12/1917 | Libby |
| 1,268,544 A | 6/1918 | Cates |
| 1,470,710 A | 10/1923 | Davis |
| 1,495,675 A | 5/1924 | Colt |
| 1,598,224 A | 8/1926 | Van Sant |
| 1,658,706 A | 2/1928 | Carrott |
| D75,971 S | 8/1928 | Faubert et al. |
| 1,704,564 A | 3/1929 | Friedland |
| 1,705,109 A | 3/1929 | Essbach |
| 1,728,956 A | 9/1929 | Darmitzel |
| 1,741,143 A | 12/1929 | Chin |
| 1,816,582 A | 7/1931 | Heron |
| 1,817,585 A | 8/1931 | Samuel |
| 1,860,924 A | 5/1932 | Cooke |
| 1,861,347 A | 5/1932 | Johnson |
| 1,872,832 A | 8/1932 | Silverberg |

(Continued)

FOREIGN PATENT DOCUMENTS

| | | |
|---|---|---|
| CH | 99738 | 6/1923 |
| CN | 99225704.2 | 11/1999 |

(Continued)

OTHER PUBLICATIONS

International Search Report Dated April 16, 2008.

*Primary Examiner* — Thomas McEvoy
(74) *Attorney, Agent, or Firm* — Ryan M. Flandro (57) ABSTRACT

An oral care implement with a soft tissue cleanser is provided to effectively cleanse the soft tissue of the mouth with comfort and a reduced risk of injury to the user. In one construction, a projection is formed of a combination of a hard material and a soft material. The rigid material provides stability for cleaning debris from the tongue or other tissue while the soft material provides comfort and a reduced risk of injury.

21 Claims, 4 Drawing Sheets

(56) References Cited

U.S. PATENT DOCUMENTS

| | | | |
|---|---|---|---|
| 1,891,864 | A | 12/1932 | Barrett |
| 1,892,068 | A | 12/1932 | Metzler |
| 1,903,161 | A | 3/1933 | Barkan |
| 2,083,217 | A | 7/1934 | Brothers et al. |
| 1,993,662 | A | 3/1935 | Green |
| 1,993,763 | A | 3/1935 | Touchstone |
| D99,352 | S | 4/1936 | Grapp |
| 2,042,239 | A | 5/1936 | Planding |
| 2,049,956 | A | 8/1936 | Greenberg |
| 2,059,914 | A | 11/1936 | Rosenberg |
| 2,079,728 | A | 5/1937 | Arnold |
| 2,129,082 | A | 9/1938 | Byrer |
| 2,161,349 | A | 6/1939 | Hadden |
| 2,186,005 | A | 1/1940 | Casto |
| D122,815 | S | 10/1940 | Crosby |
| 2,218,072 | A | 10/1940 | Runnels |
| 2,225,331 | A | 12/1940 | Campbell |
| 2,233,936 | A | 3/1941 | Campbell |
| 2,253,210 | A | 8/1941 | Psiharls |
| 2,253,910 | A | 8/1941 | Luenz |
| 2,263,802 | A | 11/1941 | Grusin |
| 2,279,355 | A * | 4/1942 | Wilensky ........................ 15/110 |
| 2,305,461 | A | 12/1942 | Spyra |
| 2,364,205 | A | 12/1944 | Fuller |
| 2,405,029 | A | 7/1946 | Gallanty et al. |
| 2,418,485 | A | 4/1947 | Shipley |
| 2,491,274 | A | 12/1949 | McNeill |
| 2,512,059 | A | 6/1950 | Haeusser |
| 2,517,912 | A | 8/1950 | Nathan |
| 2,651,068 | A | 11/1950 | Seko |
| 2,543,999 | A | 3/1951 | Voss |
| D182,941 | S | 4/1951 | Ehrman |
| 2,554,777 | A | 5/1951 | Dangin |
| 2,574,654 | A | 11/1951 | Moore |
| 2,583,750 | A | 1/1952 | Runnels |
| 2,642,604 | A | 6/1953 | Ferrari |
| 2,708,762 | A | 6/1953 | Kling et al. |
| 2,888,325 | A | 8/1954 | Silver |
| 2,702,914 | A | 3/1955 | Kittle et al. |
| 3,103,680 | A | 9/1963 | Krichmar |
| 3,153,800 | A | 10/1964 | Trotin |
| 3,181,193 | A | 5/1965 | Nobles et al. |
| 3,195,537 | A | 7/1965 | Blasi |
| 3,254,356 | A | 6/1966 | Yao et al. |
| 3,258,805 | A | 7/1966 | Rossnan |
| 3,337,893 | A | 8/1967 | Fine et al. |
| D213,669 | S | 4/1969 | Miller |
| RE26,688 | E * | 10/1969 | Lemelson .................... 15/209.1 |
| 3,509,874 | A | 5/1970 | Stillman |
| 3,610,043 | A | 10/1971 | Wemyss |
| 3,633,237 | A | 1/1972 | Bagube |
| 4,299,208 | A | 11/1981 | Blanc |
| 4,328,604 | A | 5/1982 | Adams |
| 4,358,585 | A | 11/1982 | Igarashi et al. |
| 4,364,142 | A | 12/1982 | Pangle |
| D272,683 | S | 2/1984 | Stocchi |
| D272,687 | S | 2/1984 | Stocchi |
| D272,689 | S | 2/1984 | Stocchi |
| D272,690 | S | 2/1984 | Stocchi |
| D273,635 | S | 5/1984 | Stocchi |
| 4,455,704 | A | 6/1984 | Williams |
| 4,488,327 | A | 12/1984 | Snider |
| 4,610,043 | A | 9/1986 | Vezjak |
| D287,072 | S | 12/1986 | Pfleger |
| 4,628,564 | A | 12/1986 | Youssef |
| D295,695 | S | 5/1988 | Golzari |
| 4,827,551 | A | 5/1989 | Maser et al. |
| 4,888,844 | A | 12/1989 | Maggs |
| D309,528 | S | 7/1990 | Valenti |
| 5,005,246 | A | 4/1991 | Yen-Hui |
| 5,032,082 | A | 7/1991 | Herrera |
| 5,040,260 | A | 8/1991 | Michaels |
| 5,120,225 | A | 6/1992 | Amit |
| 5,165,761 | A | 11/1992 | Dirksing |
| 5,176,427 | A | 1/1993 | Weihrauch |
| 5,224,234 | A * | 7/1993 | Arsenault et al. ............ 15/167.1 |
| 5,226,197 | A | 7/1993 | Nack et al. |
| 5,230,118 | A | 7/1993 | Chamma |
| 5,242,235 | A | 9/1993 | Li |
| 5,249,327 | A | 10/1993 | Hing |
| 5,273,425 | A | 12/1993 | Hoagland |
| 5,305,489 | A | 4/1994 | Lage |
| D350,851 | S | 9/1994 | Spence, Jr. |
| 5,392,483 | A | 2/1995 | Heinzelman et al. |
| 5,396,678 | A | 3/1995 | Bredall et al. |
| 5,438,726 | A | 8/1995 | Leite |
| 5,445,825 | A | 8/1995 | Copelan et al. |
| 5,511,273 | A | 4/1996 | Carroll |
| 5,530,981 | A | 7/1996 | Chen |
| 5,535,474 | A | 7/1996 | Salazar |
| 5,544,383 | A * | 8/1996 | Gamble ......................... 15/106 |
| 5,570,487 | A | 11/1996 | Schneider |
| D376,695 | S | 12/1996 | Tveras |
| 5,584,690 | A | 12/1996 | Maassarani |
| 5,604,951 | A | 2/1997 | Shipp |
| 5,613,262 | A | 3/1997 | Choy-Maldonado |
| 5,628,082 | A | 5/1997 | Moskovich |
| D386,905 | S | 12/1997 | Brady et al. |
| 5,709,004 | A | 1/1998 | Paduano et al. |
| D390,706 | S | 2/1998 | Hohlbein et al. |
| D391,769 | S | 3/1998 | Kling et al. |
| 5,735,011 | A | 4/1998 | Asher |
| 5,735,864 | A | 4/1998 | Heisinger, Jr. |
| 5,758,380 | A | 6/1998 | Vrignaud |
| 5,766,193 | A | 6/1998 | Millner |
| D396,288 | S | 7/1998 | Samuel |
| 5,778,475 | A | 7/1998 | Garcia |
| 5,778,476 | A | 7/1998 | Squillaci et al. |
| 5,779,654 | A | 7/1998 | Foley et al. |
| D397,219 | S | 8/1998 | Rangel et al. |
| 5,802,656 | A | 9/1998 | Dawson et al. |
| D399,349 | S | 10/1998 | Barth |
| 5,817,114 | A | 10/1998 | Anderson et al. |
| 5,818,856 | A | 10/1998 | Injeyan et al. |
| D401,069 | S | 11/1998 | Lamond et al. |
| D402,116 | S | 12/1998 | Magloff et al. |
| 5,845,358 | A | 12/1998 | Woloch |
| D403,510 | S | 1/1999 | Menke et al. |
| D404,205 | S | 1/1999 | Hohlbein |
| D404,206 | S | 1/1999 | Hohlbein |
| D405,272 | S | 2/1999 | Khalaj et al. |
| D407,221 | S | 3/1999 | Van Gelder |
| D407,222 | S | 3/1999 | Van Gelder |
| D407,223 | S | 3/1999 | Van Gelder |
| 5,875,510 | A | 3/1999 | Lamond et al. |
| 5,896,614 | A | 4/1999 | Flewitt |
| 5,913,346 | A | 6/1999 | Narwani |
| 5,915,433 | A | 6/1999 | Hybler |
| 5,920,941 | A | 7/1999 | Iannotta |
| 5,928,254 | A | 7/1999 | Jensen |
| 5,930,860 | A | 8/1999 | Shipp |
| 5,938,673 | A | 8/1999 | DePierro et al. |
| 5,946,759 | A | 9/1999 | Cann |
| 5,951,578 | A | 9/1999 | Jensen |
| 5,957,942 | A | 9/1999 | Yudelman |
| 5,967,152 | A | 10/1999 | Rimkus |
| 5,970,564 | A | 10/1999 | Inns et al. |
| 5,980,541 | A | 11/1999 | Tenzer |
| 5,980,542 | A | 11/1999 | Saldivar |
| 6,015,293 | A | 1/2000 | Rimkus |
| D420,515 | S | 2/2000 | Van Gelder |
| D421,844 | S | 3/2000 | Stark et al. |
| 6,041,467 | A | 3/2000 | Roberts et al. |
| D422,413 | S | 4/2000 | Goldinger et al. |
| D423,785 | S | 5/2000 | Karallis |
| D423,786 | S | 5/2000 | Zelinski |
| D423,787 | S | 5/2000 | Musciano |
| D424,808 | S | 5/2000 | Beals et al. |
| D424,809 | S | 5/2000 | Bernard |
| D425,306 | S | 5/2000 | Beals et al. |
| 6,058,541 | A | 5/2000 | Masterman et al. |
| D428,702 | S | 8/2000 | Van Gelder |
| 6,098,233 | A | 8/2000 | Chen |
| 6,105,191 | A | 8/2000 | Chen et al. |

| | | |
|---|---|---|
| 6,108,851 A | 8/2000 | Bredall et al. |
| 6,108,869 A | 8/2000 | Meessmann et al. |
| 6,119,296 A * | 9/2000 | Noe et al. .................. 15/104.94 |
| D434,906 S | 12/2000 | Beals et al. |
| 6,171,323 B1 | 1/2001 | Potti et al. |
| D440,767 S | 4/2001 | Moskovich et al. |
| 6,254,390 B1 | 7/2001 | Wagner |
| 6,260,227 B1 | 7/2001 | Fulop et al. |
| 6,276,021 B1 | 8/2001 | Hohlbein |
| 6,289,545 B1 | 9/2001 | Molster |
| D448,569 S | 10/2001 | Harris et al. |
| 6,308,367 B1 | 10/2001 | Beals et al. |
| 6,322,573 B1 | 11/2001 | Murayama |
| 6,345,405 B1 | 2/2002 | Brackin |
| 6,353,958 B2 | 3/2002 | Weihrauch |
| D456,139 S | 4/2002 | Hohlbein |
| 6,374,448 B2 | 4/2002 | Seifert |
| D456,607 S | 5/2002 | Carlucci et al. |
| 6,383,202 B1 | 5/2002 | Rosenblood |
| D459,087 S | 6/2002 | Pfleger |
| 6,402,768 B1 | 6/2002 | Liebel |
| 6,408,476 B1 | 6/2002 | Cann |
| 6,421,867 B1 | 7/2002 | Weihrauch |
| D461,959 S | 8/2002 | Chan et al. |
| D463,131 S | 9/2002 | Winter et al. |
| 6,446,295 B1 | 9/2002 | Calabrese |
| D464,796 S | 10/2002 | Winter et al. |
| D465,847 S | 11/2002 | Jacobs |
| 6,496,999 B1 | 12/2002 | Gleason et al. |
| 6,513,182 B1 | 2/2003 | Calabrese et al. |
| D471,276 S | 3/2003 | Potti et al. |
| 6,546,586 B2 | 4/2003 | Cho |
| 6,571,417 B1 * | 6/2003 | Gavney et al. .................. 15/117 |
| D477,465 S | 7/2003 | Reilly et al. |
| D478,211 S | 8/2003 | Ping |
| 6,625,839 B2 | 9/2003 | Fischer |
| D482,199 S | 11/2003 | De Salvo |
| 6,647,581 B1 | 11/2003 | Persad et al. |
| D483,184 S | 12/2003 | Geiberger et al. |
| D483,568 S | 12/2003 | Jamson |
| D486,649 S | 2/2004 | Sprosta et al. |
| 6,729,789 B2 | 5/2004 | Gordon |
| 6,817,054 B2 | 11/2004 | Moskovich et al. |
| 6,859,969 B2 | 3/2005 | Gavney et al. |
| D503,538 S | 4/2005 | Desalvo |
| 6,886,207 B1 | 5/2005 | Solanki |
| 6,895,629 B1 | 5/2005 | Wenzler |
| 2001/0023516 A1 | 9/2001 | Driesen et al. |
| 2001/0041903 A1 | 11/2001 | Richard |
| 2001/0042280 A1 | 11/2001 | Moskovich et al. |
| 2002/0004964 A1 | 1/2002 | Luchino et al. |
| 2002/0019645 A1 | 2/2002 | Fischer et al. |
| 2002/0108194 A1 | 8/2002 | Carlucci et al. |
| 2002/0124333 A1 | 9/2002 | Hafliger et al. |
| 2002/0124337 A1 | 9/2002 | Calabrese et al. |
| 2002/0138926 A1 | 10/2002 | Brown, Jr. et al. |
| 2002/0138928 A1 | 10/2002 | Calabrese |
| 2003/0009837 A1 | 1/2003 | Cann |
| 2003/0115699 A1 | 6/2003 | Wagstaff |
| 2003/0163149 A1 | 8/2003 | Heisinger, Jr. |
| 2003/0163884 A1 * | 9/2003 | Weihrauch .................. 15/207.2 |
| 2003/0167582 A1 | 9/2003 | Fischer et al. |
| 2003/0196283 A1 | 10/2003 | Gatzemeyer et al. |
| 2003/0208865 A1 | 11/2003 | Davies |
| 2003/0216762 A1 | 11/2003 | Levit |
| 2003/0229959 A1 | 12/2003 | Gavney, Jr. et al. |
| 2004/0006837 A1 | 1/2004 | Cann |
| 2004/0025275 A1 | 2/2004 | Moskovich et al. |
| 2004/0068810 A1 | 4/2004 | Lee |
| 2004/0134007 A1 | 7/2004 | Davies |
| 2004/0255416 A1 | 12/2004 | Hohlbein |
| 2005/0000049 A1 | 1/2005 | Hohlbein |
| 2005/0069372 A1 | 3/2005 | Hohlbein et al. |
| 2005/0210612 A1 | 9/2005 | Hohlbein et al. |
| 2006/0052806 A1 * | 3/2006 | Xi et al. ........................ 606/161 |
| 2006/0129171 A1 | 6/2006 | Moskovich |
| 2006/0230563 A1 * | 10/2006 | Gavney, Jr. ..................... 15/117 |
| 2008/0163888 A1 * | 7/2008 | Chen ............................ 132/323 |

FOREIGN PATENT DOCUMENTS

| | | |
|---|---|---|
| DE | 857 128 | 11/1952 |
| DE | 29 30 459 | 2/1981 |
| DE | 31 14 507 A1 | 3/1983 |
| DE | 38 39 424 A1 | 6/1988 |
| DE | 201 07 614 | 10/2002 |
| DE | 101 22 987 | 11/2002 |
| DE | 20 2005 009 026 | 11/2005 |
| EP | 0875169 A | 4/1998 |
| EP | 1 034 721 | 9/2000 |
| EP | 1308108 | 5/2003 |
| FR | 537979 | 6/1922 |
| FR | 2594307 | 4/1987 |
| GB | 17643 | 4/1912 |
| GB | 495982 | 11/1938 |
| GB | 2371217 | 7/2002 |
| GB | 2391462 | 2/2004 |
| JP | 2000-278899 | 10/2000 |
| JP | 2000-308522 | 11/2000 |
| JP | 2001-161720 | 6/2001 |
| JP | 2001-314232 | 11/2001 |
| JP | 2001314232 | 11/2001 |
| JP | 2002-142867 | 5/2002 |
| RU | 1708283 | 1/1992 |
| RU | 28613 | 4/2003 |
| WO | WO 96/15696 | 5/1996 |
| WO | WO 98/05241 A | 2/1998 |
| WO | Wo 98/08458 | 3/1998 |
| WO | WO 98/09573 | 3/1998 |
| WO | WO 98/22000 | 5/1998 |
| WO | WO 99/49754 A1 | 10/1999 |
| WO | WO 00/64307 | 2/2000 |
| WO | WO 01/17433 A1 | 3/2001 |
| WO | WO 01/45573 A1 | 6/2001 |
| WO | WO 01/80686 A2 | 11/2001 |
| WO | WO 02/071967 A2 | 9/2002 |
| WO | WO 03/030680 A | 4/2003 |
| WO | WO 2004/019801 A | 3/2004 |
| WO | 2006/005369 A | 1/2006 |
| WO | 2006055574 A | 5/2006 |

* cited by examiner

ORAL CARE IMPLEMENT

FIELD OF THE INVENTION

The present invention pertains to an oral care implement with a tongue cleanser or the oral care member for cleansing the tongue and other soft tissue in the mouth.

BACKGROUND OF THE INVENTION

According to the American Dental Association, bad breath in healthy people is often attributable to microbial deposits on the tongue. Due to its papillary nature, the tongue creates a unique ecological site that provides a large surface area, which favors the accumulation of oral bacteria. Anaerobic flora and bacteria residing on the tongue can lead to the development of chronic bad breath commonly called halitosis.

While tongue scrapers have been used in the past, these scrapers have not adequately met the need. Past scrapers have typically been uncomfortable, risked injury to the user, and/or lacked effectiveness. Hence, there is a need for an oral care implement with a tongue cleanser that provides effective removal of bacteria and other debris with comfort and safety.

BRIEF SUMMARY OF THE INVENTION

The present invention pertains to an oral care implement with a tongue cleanser provided with a combination of hard and soft materials to cleanse the tongue and other soft tissue within the mouth with comfort and a reduced risk of injury to the user.

In one embodiment, an oral care implement includes a head and at least one projection protruding from the head to cleanse soft tissue within a mouth of a user. The projection is formed of multiple components including a first component composed of a first material having a first hardness value and a second component composed of a second material having second hardness value. The second component overlies a portion of the first component, wherein the first and second hardness values are different. A tissue cleansing projection is provided on the second component. In yet another construction, the first hardness value is greater than the second hardness value.

In one aspect of the invention, a toothbrush includes a projection having a base with a tip remote from the head to engage and clean the soft tissue, and a soft material component overlies at least the tip of the base and the second component includes a tissue cleaning projection extending from the second component.

In one embodiment, a tongue cleanser is formed of two components that combine to define at least one cleaning projection that extends from a head of an implement. One component of the tongue cleanser is composed of a relatively hard material to provide stability and effective cleaning of the soft tissue. The other component is composed of a relatively soft material to provide comfort and safety to the user during use of the implement.

DETAILED DESCRIPTION OF THE INVENTION

Figure 1:
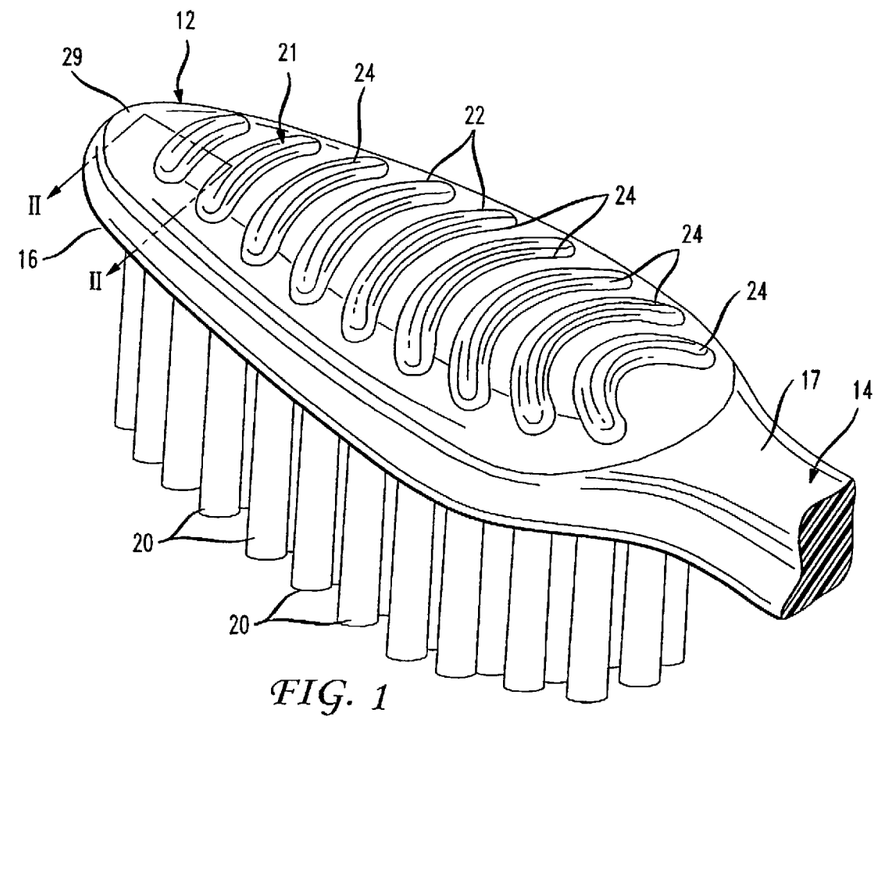
FIG. 1 is a perspective views of a head of a toothbrush in accordance with the present invention.
Figure 2:
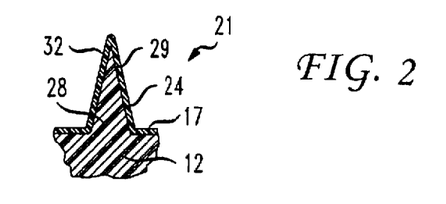
FIG. 2 is a partial cross-sectional view taken along line II-II in FIG. 1.

An oral care implement in accordance with the present invention is illustrated and described in the form of a toothbrush 10 (FIGS. 1 and 2). Nevertheless, the invention could be encompassed into other oral care implements, including simply a tissue-cleansing implement. Toothbrush 10 includes a head 12 and a handle 14. While FIG. 1 only illustrates the connection of the handle to the head, the handle is preferably an elongate member to be grasped by the user. The handle 14 could have any known shape and construction adapted for the manipulation needed to clean the teeth and/or tongue of a user. Head 12 includes a pair of opposite sides 16, 17 with teeth cleaning elements 20 extending from side 16 and a soft tissue cleanser 21 provided on side 17. While such soft tissue cleanser 21 may be used to impact areas of the mouth other than the teeth, it is primarily intended for use as a tongue cleanser and will be described herein as such for purposes of convenience. Although head 12 is shown with an oblong shape, other known shapes could be used.

The teeth cleaning elements 20 could be bristles and/or elastomeric members of various shapes and sizes. Any form or combination of elements 20 suitable for cleaning a user's teeth could be used.

Tongue cleanser 21 includes at least one projection 22, and preferably a plurality of projections, to cleanse the tongue and other soft tissue of the mouth (e.g., the inner surfaces of the cheeks). While the projections are preferably formed on a head also provided with teeth cleaning elements 20, they could be formed on other implements or other parts of the toothbrush. Any reference to a head of an implement is simply meant to be a reference to the operative portion of the implement that is inserted into the mouth, and does not refer to a particular shape, structure or location of the head. In the present invention, each of the projections is formed by a combination of hard and soft materials to provide the beneficial effects of superior cleaning of the tongue (or other soft tissue) with comfort and safety from injury.

In one embodiment (FIGS. 1 and 2), a plurality of projections 22 are formed to extend across a back side 17 of head 12. Each projection includes a base portion 28 protruding from the head, and a layer 29 overlying the base portion (FIG. 2). Base 28 is composed of a relatively rigid material such as polypropylene, although many other materials could be used. The base portion is preferably formed as part of the head as shown in FIG. 2, but could be separately formed and attached to the head by adhesive, fasteners or the like. Layer 29 is preferably a thermoplastic elastomer such as Santoprene, although many other materials could also be used so long as they are compatible for oral care and soft enough to provide the desired comfort and/or safety benefits. While projections 22 are described and shown as ridges 24, they could have a non-ridge construction (e.g., columnar or conical) if desired. Various shapes and cross-sectional configurations of projections 22 are contemplated.

Figure 3:
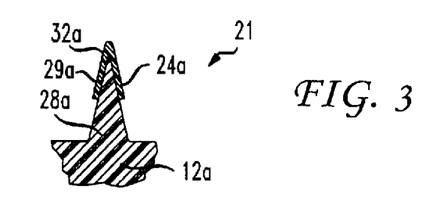
FIGS. 3-6 are partial cross sectional views alternative structures taken along line II-II of FIG. 1.

In this one construction, base 28 tapers to a narrow tip 32 to better dig into the recesses in the tongue and remove bacteria and debris. As shown, the base can be formed to have a generally triangular cross section, though other narrowing shapes could be used. Moreover, constant cross-sectional shapes, non-tapering shapes or those that do not taper to a narrow tip could also be used if desired. The soft overlayer 29 overlies the entire back side 17 of head 12 for enhanced comfort and safety; i.e., layer 29 protects users from cutting or injuring their tongues or other tissue even when very narrow tips are used to define ridges 24. Soft layer 29 is preferably molded over side 17 of head 12, but could be otherwise secured such as by adhesive, fasteners, etc. Alternatively, a soft layer or covering 29a could be formed to cover only the tips 32a of ridges 24a of tongue cleanser 21a (FIG. 3). Of course, other variations in coverage of the projections by overlayer 29 could be used. For example, the soft material component 29 could cover more or less of the base 28 than is shown in FIG. 3, or could cover bases 28 and only a part of side 17 of head 12 without covering the entire side. In one example, base 28 extends 0.5 to 1.0 mm from side 17 of head 12, and soft material component 29 is 0.3 to 0.5 mm thick. Nevertheless, many other smaller and greater extensions and thicknesses could be used to form projections.

Figure 4:
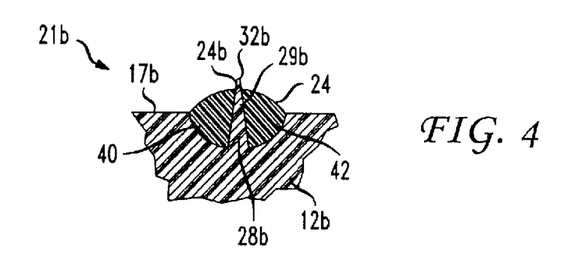

In another embodiment (FIG. 4), tongue cleanser 21a includes at least one ridge 24b defined by a base portion 28b and an overlayer 29b. As with the earlier embodiment, base 28b is formed of a relatively hard material, which in the preferred construction is formed as a unitary portion of the head. As with the earlier embodiment, base 28b preferably tapers to a narrow tip 32b to effectively remove bacteria and debris, although other shapes could be used. Overlayer 29b is composed of a relatively soft material, which partially covers base portion 28b. In this construction, the tip 32b of base portion 28b is left uncovered, while the remaining portion of the base is covered by the soft component 29b. Nevertheless, comfort and safety are maintained with the exposed tip 32b, even when narrowed, by limiting the extension of the exposed tip beyond the soft material 29b. More specifically, tongues or other soft tissue within the mouth tend to give or flex as the ridges contact and move over them. This flexibility enables a short tip 32b to pass over the tongue or other tissue without injuring the user. As a result, comfort and safety are maintained.

In one such construction, base portion 28b protrudes outward from a recess 40 formed in side 17b of head 12b. In this example, since base 28b is formed as an elongate ridge, recess 40 has the form of an elongate channel extending across side 17b. If the projection were instead, for example, columnar, the recess would then preferably encircle the projection. The soft component 29b fills and is secured in recess 40 about base 28, and defines an outer surface 42 that gradually extends to a position proximate tip 32b. In the illustrated example, outer surface 42 of overlayer 29 has a broad curved, convex shape against which the tongue or other tissue slides. This outer surface, however, could have many different shapes so long as it provides a surface against which the tongue or other tissue can slide and be exposed to only a small portion of the underlying base 28b. In this one example shown in FIG. 4, base 28b has a height (i.e., from the bottom of recess 40 to tip 32b) of 1.0 mm, and extends 0.5 mm beyond outer surface 42, though these dimensions could vary considerably. Moreover, the construction could vary. For example, recess 40 could be eliminated and the hard component formed as a shorter base that extends directly from a generally planar back side 17. In this construction, soft component would preferably be a generally uniform layer overlying at least part of the back side of the head and part of the base. Also, alternatively, the tip portion of the relatively hard first component could be secured to the relatively soft second component (not shown) rather than the being directly fixed to the head.

In another embodiment (FIG. 5), tongue cleanser 21c is formed by a soft material component 29c that defines a projection 48 which is embedded in a relatively hard base 49, preferably a hard base portion of head 12c. In this construction, projection 48 preferably protrudes from a recess 50 defined in side 17c of head 12c; although recess 50 could be omitted. Projection 48 preferably extends outwardly from the recess 50 and above a plane 55 defined by the side 17c such that the projection 48 is raised relative to the side 17c to provide increased cleaning benefits. Nevertheless, tip 56 of the projection may be generally co-extensive with plane 55 so long as contact with the soft tissue still occurs. Recess 50 is similar to recess 40 discussed above, except that in this construction the recess remains open. In this example, since the projection is formed as an elongate ridge, recess 50 would be an elongate channel extending across the head. Ridge 48 is anchored into the head to provide a stiffer member, despite being a soft material to provide an effective cleansing of the tongue and other tissue. In the illustrated example, ridge 48 has a height (extending from the bottom of recess 50) of about 1.0 mm, and a projection above back side 17c of about 0.50 mm. Nevertheless, wide variations from these dimensions may be used.

Figure 5:
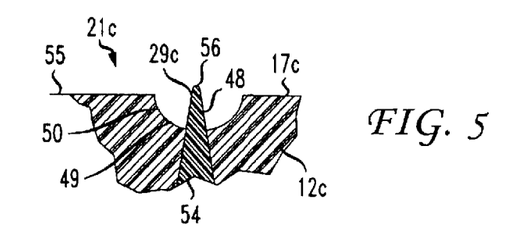

In the one construction, projection 48 includes an anchoring portion 54 that is embedded in base 49 (which is preferably a portion of head 12) and a tip 56 for contacting the soft tissue. Projection 48 preferably tapers from anchoring portion 54 to tip 56 to define a narrowed tip for effectively cleaning of the tongue and other tissue, and a broad anchoring portion for greater support and stiffness. Nevertheless, other tapering and non-tapering projections could be used.

Figure 6:
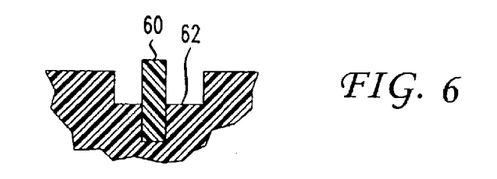

Furthermore, the construction of FIG. 5 illustrates one example of a concavity defined within side 17c (i.e., the recess 50) that includes a tissue-cleaning convexity (i.e., projection 48) extending outwardly therefrom. As noted above, the concavity can be defined as an elongate depression or ridge or a hemispherical recess, with other concavities being contemplated. In addition, the convexity can be any shape and/or cross-section including, but not limited to, those projection shapes disclosed herein. For instance, the convexity can be a column 60 of constant cross-section extending from a concavity 62 of square profile as shown in FIG. 6.

Figure 7:
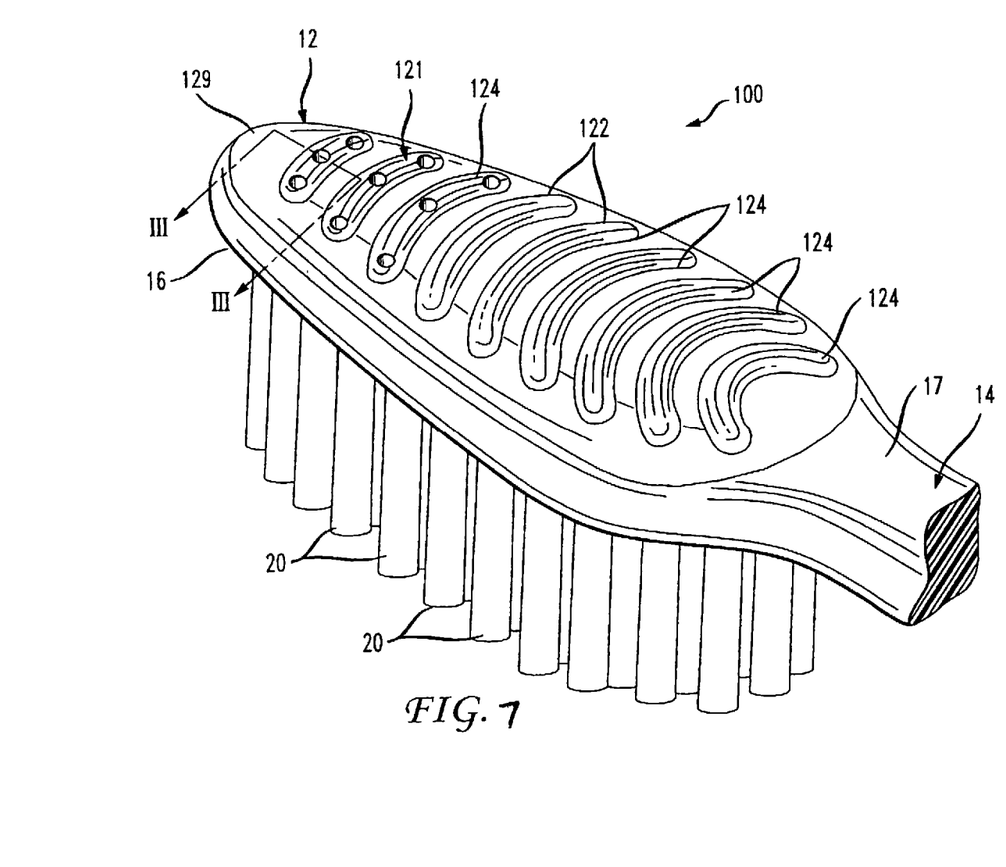
FIG. 7 is a perspective view of an alternative head of a toothbrush in accordance with the present invention.
Figure 8:
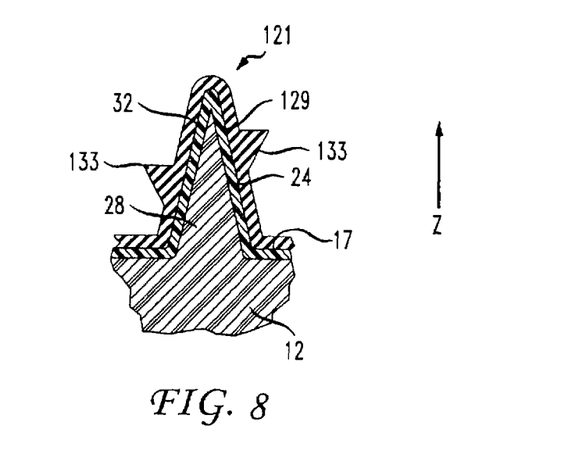
FIG. 8-9 are partial cross sectional views alternative structures taken along line III-III of FIG. 7.

In one construction shown in FIGS. 7-8, a toothbrush 100 includes a head and at least one compound projection protruding from the head to cleanse soft tissue within a user's mouth. The projection is formed of two components including a first component composed of a first material having a first hardness value and a second component composed of a second material has second hardness value. The second component overlies a portion of the first component. The first and second hardness values are different to provide oral care benefits. In yet another construction shown in FIG. 7, the first hardness value is greater than the second hardness value.

In one construction of toothbrush 100 shown in FIG. 7, the first material can be the hardened plastic section (specifically in the head) covered with a soft thermoplastic elastomer (TPE/rubber) serving as the second material. The head section has an irregular surface or set of features that when covered with the soft TPE material collectively forms a tissue cleanser 121. Tissue cleanser 121 includes at least one compound projection 122, and preferably a plurality of compound projections, to cleanse the tongue and other soft tissue of the mouth (e.g., the inner surfaces of the cheeks). In addition, other ridge or projection constructions could be used. For example, the ridges could be linear instead of curved or include a mixture of curved and linear ridges. The ridges could be non-concentric or curved at all the same radius of curvature. Moreover, while the ridges preferably extend substantially across the side of head 12, they could extend only part way across the head.

While the projections 122 are formed on a head also provided with teeth cleaning elements 20, they could be formed on other implements or other parts of the toothbrush 100, such as on the handle for gripping. Any reference to a head of an implement is simply meant to be a reference to the operative portion of the implement that is inserted into the mouth, and does not refer to a particular shape, structure or location of the head. In the present invention, each of the projections is formed by a combination of hard and soft materials to provide the beneficial effects of superior cleaning of the tongue (or other soft tissue) with comfort and safety from injury. The tissue cleanser 121 has an enhanced surface that can be used for tongue and soft tissue cleaning during the brushing task. The tissue cleanser 121 is further enhanced by adding a combination of ribs, cones, or other textures to improve the cleaning capability of the irregular surface.

Figure 9:
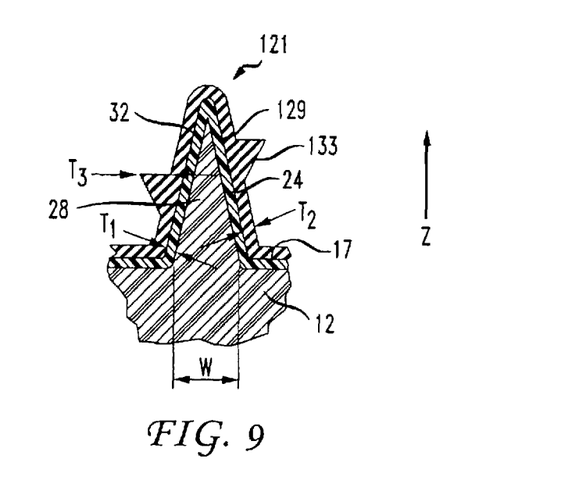

In one construction (FIGS. 7-9), a plurality of projections 122 are formed to extend across a back side 17 of head 12. Each projection includes a base portion 128 protruding from the head, a first layer 129 overlying the base portion (FIG. 8), and a second layer 131 extending from the first layer 129. Base portion 128 is composed of a relatively rigid material such as polypropylene, although many other materials could be used. The base portion is preferably formed as part of the head as shown in FIG. 7, but could be separately formed and attached to the head by adhesive, fasteners or the like. Layers 129, 131 are a thermoplastic elastomer such as Santoprene, although many other materials could also be used so long as they are compatible for oral care and soft enough to provide the desired comfort and/or safety benefits. To provide comfort as well as cleaning benefits, the elastomeric material preferably has a hardness property (e.g., durometer value) in the range of A8 to A25 Shore hardness. Nevertheless, material from other manufacturers or other materials within and outside the noted hardness range could be used. It should be noted that the durometer value of the base portion 128 is greater than the durometer value of the thermoplastic elastomer from the layers 129, 131 and component 133.

Referring to FIG. 8, in one example, base 28 extends (W) 0.5 to 1.0 mm from side 17 of head 12. The soft material component layers 129, 131 are for example, 0.2 to 0.5 mm thick (T1), (T2), respectively, and the soft material component 133 extends from the layer 131 about 0.2 mm (T3). Nevertheless, many other smaller and greater extensions and thicknesses could be used to form projections for cleaning the tongue, for example. To be more efficient manufacturing, a ratio of the collective thickness of the layers 129, 131 to the width of the base 28 is less than 1.0 and between 0.20 to 0.9 (e.g., (T1+T2)/W<1.0 to 0.20). As noted the FIG. 9, the ratio may vary as the width of the base changes. For example, at the lowest most part of the base 28, width has the greatest value. Traveling up the vertical axis of the rigid base 28, the width becomes smaller. In another embodiment, a ratio of the collective thickness of the layers 129, 131, and projection 133 to the width of the base 28 is best less than 1.0 (e.g., (T1+T2+T3)/W<1.0.). In this way, management of the noted ratios can provide cost effective toothbrush configurations as well as comfort and cleaning benefits. With regard to the first component and second component hardness values, the projection 121 has a blended section modulus as the tips may blend slightly along the longitudinal axis. The features of FIGS. 7-9 can be applied to the embodiments shown in FIGS. 1-6 so that compound projection can be formed.

Although the tongue or tissue cleanser of the present invention has been discussed primarily in connection with a plurality of ridges that extend laterally across the head, the concepts of the invention are applicable to all kinds of projections usable as a tongue cleanser. For example, the ridges may have all kinds of shapes and configurations on the head as disclosed in co-pending U.S. patent application Ser. No. 10/989,267, entitled Oral Care Implement, filed Nov. 17, 2004, which is hereby incorporated by reference. Moreover, the projections may be formed as non-ridge projections or a mixture of ridge and non-ridge projections.

Also various other changes could be made in the above disclosed constructions without departing from the scope of the invention, it is intended that all matter contained in this application, including all mechanisms and/or modes of interaction described above, shall be interpreted as illustrative only and not limiting in any way the scope of the appended claims.

The invention claimed is:

1. An oral care implement comprising a head having:
a first surface and a second surface opposite the first surface,
a plurality of bristles extending from the second surface of the head to clean teeth,
at least one compound projection protruding outward from the first surface of the head to cleanse soft tissue within a mouth of a user, the compound projection being formed of multiple components including:
a base composed of a first material having a first hardness value,
a first layer composed of a second material having a second hardness value, the first layer overlying a portion of the base, and
a second layer overlying at least a portion of the first layer, the second layer composed of the second material and having a tissue cleaning projection protruding therefrom,
wherein the first and second hardness values are different, and
wherein the tissue cleaning projection is formed of the second material and integral with the second layer.

2. An oral care implement in accordance with claim 1, wherein the first hardness value is greater than the second hardness value.

3. An oral care implement in accordance with claim 1, wherein the base has a width and the tissue cleaning projection has a first thickness, the first layer has a second thickness and the second layer has a third thickness; wherein the sum of the first thickness, the second thickness and the third thickness divided by the width of the base defines a ratio of less than 1.0.

4. An oral care implement in accordance with claim 3, wherein the tissue cleaning projection tapers to form a tip to clean the soft tissue.

5. An oral care implement in accordance with claim 3, wherein the second layer includes a plurality of the tissue cleaning projections extending therefrom.

6. An oral care implement in accordance with claim 3, wherein the first and second layers are a soft thermoplastic elastomer.

7. An oral care implement in accordance with claim 3, wherein the base protrudes from the first surface of the head, and the first layer overlies substantially the entire first surface of the head.

8. An oral care implement in accordance with claim 1, wherein the base tapers to form a tip to engage and clean the soft tissue, and the first layer overlies substantially the entire base.

9. An oral care implement in accordance with claim 8 wherein the first surface of the head includes a recess in the form of a transverse elongate channel into which a portion of the first layer is secured.

10. An oral care implement in accordance with claim 8 wherein the first and second layers are composed of a thermoplastic elastomer.

11. An oral care implement in accordance with claim 1 wherein the head is constructed of the first material, and wherein the base is integrally formed as a unitary portion of the head.

12. An oral care implement in accordance with claim 1 wherein the base is composed of a hard plastic material.

13. An oral care implement in accordance with claim 12 wherein the first and second layers are composed of a thermoplastic elastomer.

14. An oral care implement in accordance with claim 1 wherein the first and second layers are composed of a thermoplastic elastomer.

15. An oral care implement in accordance with claim 1 wherein the tissue cleaning projection protrudes from a side surface of the compound projection in a direction generally co-extensive with the first surface of the head.

16. An oral care implement in accordance with claim 1 comprising a plurality of the compound projections on the first surface of the head.

17. An oral care implement in accordance with claim 1, wherein the compound projection further comprises a plurality of side surfaces; wherein said tissue cleaning projection comprises a first tissue cleaning projection protruding from one of the side surfaces of the compound projection; and said oral care implement further comprises a second tissue cleaning projection protruding from another of the side surfaces of the compound projection.

18. An oral care implement in accordance with claim 1, wherein the tissue cleaning projection comprises:
   a top surface substantially parallel to the first surface; and
   a side surface that is angled with respect to the the first surface.

19. An oral care implement comprising:
   a head and at least one compound projection protruding outward from a first surface of the head to cleanse soft tissue within a mouth of a user, the compound projection having side surfaces that extend outward from the first surface of the head, the compound projection being formed of multiple components including:
      a base composed of a first material having a first hardness value,
      a first layer composed of a second material having a second hardness value, the first layer overlying a portion of the base, and
      a second layer overlying at least a portion of the first layer, the second layer composed of the second material and having at least one tissue cleaning projection protruding therefrom,
   wherein the at least one tissue cleaning projection is formed of the second material and integral with the second layer,
   wherein the first and second hardness values are different; and
   teeth cleaning elements extending from a second surface of the head that is opposite the first surface of the head.

20. An oral care implement in accordance with claim 19, wherein said at least one tissue cleaning projection comprises:
   a first tissue cleaning projection protruding from one of the side surfaces of the compound projection in a spaced apart manner from the first surface of the head at a first distance from the first surface; and
   a second tissue cleaning projection protruding from another of the side surfaces of the compound projection that is opposite the one of the side surfaces in a spaced apart manner from the first surface of the head at a second distance from the first surface; and
   wherein the first distance is different than the second distance.

21. An oral care implement in accordance with claim 19, wherein the at least one tissue cleaning projection comprises:
   a top surface substantially parallel to the first surface; and
   a side surface that is angled with respect to the the first surface.

* * * * *